(12) United States Patent
Banerji

(10) Patent No.: US 12,390,465 B2
(45) Date of Patent: *Aug. 19, 2025

(54) COUMARIN DERIVATIVE FOR THERAPY OR PROPHYLAXIS OF A CELL PROLIFERATIVE DISORDER

(71) Applicants: The Institute of Cancer Research: Royal Cancer Hospital, London (GB); The Royal Marsden NHS Foundation Trust, London (GB)

(72) Inventor: Udai Banerji, London (GB)

(73) Assignees: The Institute of Cancer Research: Royal Cancer Hospital, London (GB); The Royal Marsden NHS Foundation Trust, London (GB)

(*) Notice: Subject to any disclaimer, the term of this patent is extended or adjusted under 35 U.S.C. 154(b) by 285 days.

This patent is subject to a terminal disclaimer.

(21) Appl. No.: 17/850,463

(22) Filed: Jun. 27, 2022

(65) Prior Publication Data

US 2023/0012116 A1    Jan. 12, 2023

Related U.S. Application Data

(63) Continuation of application No. 16/764,242, filed as application No. PCT/EP2018/062805 on May 16, 2018, now Pat. No. 11,400,090.

(30) Foreign Application Priority Data

Nov. 16, 2017 (WO) ............ PCT/EP2017/079506

(51) Int. Cl.
  *A61K 31/506* (2006.01)
  *A61K 9/00* (2006.01)
  *A61P 35/00* (2006.01)

(52) U.S. Cl.
  CPC .......... *A61K 31/506* (2013.01); *A61K 9/0053* (2013.01); *A61P 35/00* (2018.01)

(58) Field of Classification Search
  CPC ..... A61K 31/506; A61K 31/573; A61K 31/37
  USPC ..................................... 514/269
  See application file for complete search history.

(56) References Cited

U.S. PATENT DOCUMENTS

| 11,400,090 | B2 | 8/2022 | Banerji |
| 2010/0004233 | A1 | 1/2010 | Iikura et al. |
| 2011/0092700 | A1* | 4/2011 | Iikura .............. C07D 417/12 544/94 |
| 2014/0038920 | A1 | 2/2014 | Ballabio et al. |
| 2021/0330670 | A1 | 10/2021 | Banerji |

FOREIGN PATENT DOCUMENTS

| EP | 1982982 A1 | 10/2008 |
| EP | 2172198 A1 | 4/2010 |
| WO | WO-2001/017984 A1 | 3/2001 |
| WO | WO-2007/091736 A1 | 8/2007 |
| WO | WO-2009/014100 A1 | 1/2009 |

OTHER PUBLICATIONS

"Phase I Trial of VS-6766 alone or in combination with everolimus (RAF/MEK)," Study Record Version 1, NCT02407509, Apr. 2, 2015.
"A Dose-Escalation Study of RO5126766 in Patients With Advanced Solid Tumors," ClinicalTrials.gov Identifier: NCT00773526, Oct. 16, 2008.
"Phase I Trial of RO5126766 Alone and in Combination With Everolimus (DDU RAF/MEK)," ClinicalTrials.gov Identifier: NCT02407509, Apr. 3, 2015.
Akinleye et al., "MEK and the inhibitors: from bench to bedside," Journal of Hematology & Oncology, 6:27 (11 pages) (2013).
Aoki et al., "Optimizing the Physicochemical Properties of Raf/MEK Inhibitors by Nitrogen Scanning," ACS Med Chem Lett, 5(4): 309-314 (2014).
ASCO web page providing information on when the 2017 ASCO Annual Meeting abstracts were published, http://abstracts.asco.org/199/IndexView_199.html.
Bhatt et al., "In silico docking studies of Lupeol with MAPK pathway proteins-Raf-1, MEK & ERK," Journal of Experimental Therapeutics and Oncology, 12(2): 137-140 (2017).

(Continued)

*Primary Examiner* — Yevgeny Valenrod
(74) *Attorney, Agent, or Firm* — Foley Hoag LLP; David P. Halstead; Alexander J. Chatterley

(57) ABSTRACT

The present invention provides a method for the treatment or prevention of a cell proliferative disorder, the method comprising:

(a) administering a compound represented by formula (I):

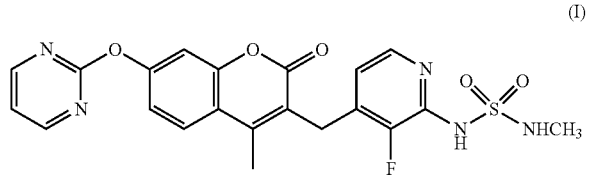

or a pharmaceutically acceptable salt thereof twice weekly for 3 weeks, (b) pausing administration of said compound or salt for the following 1 week, and (c) subsequently repeating steps (a) and (b) at least once.

21 Claims, 3 Drawing Sheets

(56) References Cited

OTHER PUBLICATIONS

Certificate submitted on Nov. 15, 2018 and Nov. 16, 2018 in Japanese Patent Application No. 2018-560956 and Japanese Patent Application No. 2018-216023 regarding a presentation given at the 2017 ASCO Annual Meeting, 4 pages.
Certificate submitted on Nov. 15, 2018 and Nov. 16, 2018 in Japanese Patent Application No. 2018-560956 and Japanese Patent Application No. 2018-216023 regarding an abstract published in relation to the 2017 ASCO Annual Meeting, 4 pages.
Chenard-Poirier et al., "Meeting Library | Results from the biomarker-driven basket trial of RO5126766 (CH5127566), a potent RAF/MEK inhibitor, in RAS- or RAF-mutated malignancies including multiple myeloma," Retreived on internet <https://meetinglibrary.asco.org/record/144582/abstract>: 2 pages (2017).
Chenard-Poirier et al., "Results from the biomarker-driven basket trial of RO5126766 (CH5126766), a potent RAF/MEK inhibitor, in RAS- or RAF-mutated malignancies, including multiple myeloma," Presentation slides for the 53rd Annual Meeting of the American Society of Clinical Oncology, (2017).
Chenard-Poirier et al., "Results from the biomarker-driven basket trial of RO5126766 (CH5127566), a potent RAF/MEK inhibitor, in RAS- or RAF-mutated malignancies including multiple myeloma," Journal of Clinical Oncology, 35(15) (2017).
Harris et al., "Updated efficacy and safety results from the phase I study of intermittent dosing of the dual MEK/RAF inhibitor, RO5126766 in patients (pts) with RAS/RAF mutated advanced solid tumours," Journal of Clinical Oncology, 34: 15 (2016).
Honda et al., "Phase I and pharmacokinetic/pharmacodynamic study of RO5126766, a first-inclass dual Raf/MEK inhibitor, in Japanese patients with advanced solid tumors," Cancer Chemother Pharmacol, 72(3): 577-584 (2013).
International Search Report and Written Opinion for International Application No. PCT/EP2018/062805 dated Aug. 16, 2018.
Ishii et al., "Enhanced Inhibition of ERK Signaling by a Novel Allosteric MEK Inhibitor, CH5126766, That Suppresses Feedback Reactivation of RAF Activity," Cancer Research, 73(13): 4050-4060 (2013).
Kraeber-Bodere et al., "Differences in the Biologic Activity of 2 Novel MEK Inhibitors Revealed by 18F-FDG PET: Analysis of Imaging Data from 2 Phase I Trials," The Journal of Nuclear Medicine, 53(12): 1836-1846 (2012).
Lito et al., "Disruption of CRAF-Mediated MEK Activation Is Required for Effective MEK Inhibition in KRAS Mutant Tumors," Cancer Cell, 25(5): 697-710 (2014).
Martinez-Garcia et al., "First-in-Human, Phase I Dose-Escalation Study of the Safety, Pharmacokinetics, and Pharmacodynamics of RO5126766, a First-in-Class Dual MEK/RAF Inhibitor in Patients with Solid Tumors," Clinical Cancer Research, 18(17): 4806-4819 (2012).
Miller et al., "MEK1/2 inhibitors in the treatment of gynecologic malignancies," Gynecologic Oncology, 133(1): 128-137 (2014).
Tanaka et al., "MEK inhibitors as a novel therapy for neuroblastoma: Their in vitro effects and predicting their efficacy," Journal of Pediatric Surgery, 51(12): 2074-2079 (2016).
Tegnebratt et al., "[18F]FDG-PET imaging is an early noninvasive pharmacodynamic biomarker for a first-in-class dual MEK/Raf inhibitor, RO5126766 (CH5126766), in preclinical xenograft models," EJNMMI Research, 3:67 (11 pages) (2013).
Ueyama et al., "Inhibition of MEK1 Signaling Pathway in the Liver Ameliorates Insulin Resistance," Journal of Diabetes Research, Article ID 8264830 (13 pages) (2016).
Van Dort et al., "Dual inhibition of allosteric mitogenactivated protein kinase (MEK) and phosphatidylinositol 3-kinase (PI3K) oncogenic targets with a bifunctional inhibitor," Bioorg Med Chem, 23(7): 1386-1394 (2015).
Wada et al., "The Dual RAF/MEK Inhibitor CH5126766/RO5126766 May Be a Potential Therapy for RAS-Mutated Tumor Cells," PLoS One, 9(11): e113217 (16 pages) (2014).

* cited by examiner

COUMARIN DERIVATIVE FOR THERAPY OR PROPHYLAXIS OF A CELL PROLIFERATIVE DISORDER

RELATED APPLICATIONS

This application is a continuation of U.S. patent application Ser. No. 16/764,242, filed May 14, 2020, which is a 371 U.S. National Stage Application of International Patent Application No. PCT/EP2018/062805, filed May 16, 2018, which claims the benefit of priority to International Patent Application No. PCT/EP2017/079506, filed Nov. 16, 2017. PCT/EP2018/062805 is hereby incorporated by reference herein in its entirety.

TECHNICAL FIELD

The present invention relates to a therapeutic or prophylactic medicament for a cell proliferative disorder, particularly cancer, comprising a coumarin derivative.

BACKGROUND ART

The compound represented by formula (I) below (also referred to herein as "compound (I)") and pharmaceutically acceptable salts thereof (also referred to herein simply as "salts thereof") are known to have pharmacological activity such as antitumor activity (see patent document 1 or 2).

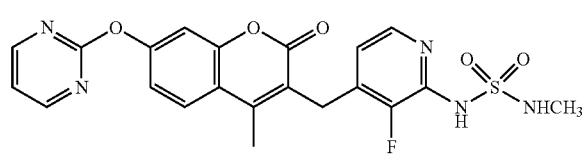

(I)

In regard to the usage and dosage of compound (I) or a salt thereof, a potassium salt of compound (I) is known to be administered to patients with solid cancers such as non-small-cell lung cancer, ovarian cancer, endometrial cancer, and colorectal cancer twice weekly at a dose of 4 mg per administration (see non patent document 1).

CITATION LIST

Patent Literature

Patent document 1: WO 2007/091736
Patent document 2: WO 2009/014100

Non Patent Literature

Non patent document 1: Journal of Clinical Oncology 34, no. 15_suppl (May 2016) 2582-2582

SUMMARY OF INVENTION

Technical Problem

When compound (I) or a salt thereof was administered according to the dosing regimen described above (twice weekly, 4 mg per administration), there were some cases where worsening of skin rash, for example, resulted in unplanned dose interruption and/or dose reduction before administration was further continued.

The present invention has been made in light of such circumstances. It is an object of the present invention to provide a dosing regimen for compound (I) or a salt thereof that can be implemented safely and for long periods, as well as a therapeutic or prophylactic medicament for a cell proliferative disorder (particularly cancer) that is used based on such a dosing regimen.

Solution to Problem

The present invention provides medicaments according to the following items A1 to A15.

A1: A medicament for the treatment or prevention of a cell proliferative disorder, the medicament comprising as an active ingredient a compound represented by formula (I):

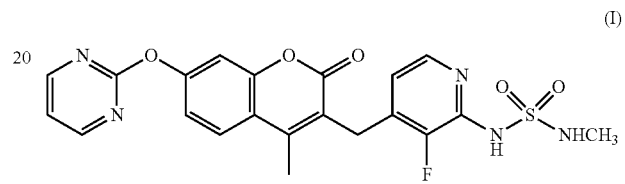

(I)

or a pharmaceutically acceptable salt thereof, wherein the medicament is used in such a manner that:
- (a) said compound or salt is administered twice weekly for 3 weeks,
- (b) administration of said compound or salt is paused for the following 1 week, and
- (c) steps (a) and (b) are subsequently repeated at least once.

A2: The medicament according to item A1, comprising a potassium salt of a compound represented by formula (I) as an active ingredient.

A3: The medicament according to item A1 or A2, wherein the cell proliferative disorder is cancer.

A4: The medicament according to any one of items A1 to A3, wherein the cell proliferative disorder is a KRAS mutant cancer.

A5: The medicament according to any one of items A1 to A4, wherein the cell proliferative disorder is a solid cancer.

A6: The medicament according to any one of items A1 to A5, wherein the dose per administration in step (a) is 3.2 mg.

A7: The medicament according to item A6, wherein the medicament is used in such a manner that prior to step (a):
- (1) said compound or salt is administered twice weekly at a dose of 3.2 mg per administration; or
- (2)
- (2a) said compound or salt is administered twice weekly for 3 weeks at a dose of 4 mg per administration,
- (2b) administration of said compound or salt is paused for the following 1 week, and
- (2c) steps (2a) and (2b) are subsequently repeated at least once.

A8: The medicament according to item A7, wherein the medicament is used in such a manner that prior to step (1) or (2), said compound or salt is administered twice weekly at a dose of 4 mg per administration.

A9: The medicament according to any one of items A1 to A5:
- (R1) wherein the medicament is used in such a manner that:
  - (A) first, said compound or salt is administered twice weekly at a dose of 4 mg per administration, (B1) next, said compound or salt is administered twice weekly at a dose of 3.2 mg per administration,
(C) after which:
(Ca) said compound or salt is administered twice weekly for 3 weeks at a dose of 3.2 mg per administration,
(Cb) administration of said compound or salt is paused for the following 1 week, and
(Cc) steps (Ca) and (Cb) are subsequently repeated at least once; or
(R2) wherein the medicament is used in such a manner that:
(A) first, said compound or salt is administered twice weekly at a dose of 4 mg per administration,
(B2) following which:
(B2a) said compound or salt is administered twice weekly for 3 weeks at a dose of 4 mg per administration,
(B2b) administration of said compound or salt is paused for the following 1 week, and
(B2c) steps (B2a) and (B2b) are subsequently repeated at least once; or
(R3) wherein the medicament is used in such a manner that:
(A) first, said compound or salt is administered twice weekly at a dose of 4 mg per administration,
(B2) following which:
(B2a) said compound or salt is administered twice weekly for 3 weeks at a dose of 4 mg per administration,
(B2b) administration of said compound or salt is paused for the following 1 week, and
(B2c) steps (B2a) and (B2b) are subsequently repeated at least once,
(C) after which:
(Ca) said compound or salt is administered twice weekly for 3 weeks at a dose of 3.2 mg per administration,
(Cb) administration of said compound or salt is paused for the following 1 week, and
(Cc) steps (Ca) and (Cb) are subsequently repeated at least once.

A10: The medicament according to any one of items A1 to A4, wherein the cell proliferative disorder is multiple myeloma.

A11: The medicament according to item A10, wherein the dose per administration in step (a) is 4 mg.

A12: The medicament according to item A10 or A11, wherein the cell proliferative disorder is an NRAS mutant cancer.

A13: The medicament according to any one of items A10 to A12, wherein the medicament is used in combination with dexamethasone, and wherein the medicament is used in such a manner that said compound or salt is administered before, simultaneously with or after administration of dexamethasone.

A14: The medicament according to item A13, wherein dexamethasone is administered once weekly at a dose of 20 mg per administration.

A15: The medicament according to any one of items A1 to A14, wherein the administration of said compound or salt is oral administration.

The medicament of the present invention may consist of compound (I) or a salt thereof, or it may be a pharmaceutical composition further comprising another component.

According to the present invention, there are also provided medicaments according to the following items A16 and A17.

A16: A medicament for the treatment or prevention of a cell proliferative disorder, the medicament comprising a compound represented by formula (I):

$$(I)$$

or a pharmaceutically acceptable salt thereof as an active ingredient, wherein the medicament is packaged together with:
(i) a container for housing said medicament, and
(ii) an instruction for using said medicament in such a manner that:
(a) said compound or salt is administered twice weekly for 3 weeks,
(b) administration of said compound or salt is paused for the following 1 week, and
(c) steps (a) and (b) are subsequently repeated at least once.

A17: The medicament according to item A16, wherein the medicament is a medicament according to any one of A1 to A15, and wherein the instruction is an instruction for using said medicament in such a manner that said compound or salt is administered according to the prescribed dosing regimen corresponding to the medicament used.

According to the present invention, there are also provided methods according to the following items B1 to B15.

B1: A method for the treatment or prevention of a cell proliferative disorder, the method comprising:
(a) administering a compound represented by formula (I):

$$(I)$$

or a pharmaceutically acceptable salt thereof twice weekly for 3 weeks,
(b) pausing administration of said compound or salt for the following 1 week, and
(c) subsequently repeating steps (a) and (b) at least once.

B2: The method according to item B1, wherein a potassium salt of a compound represented by formula (I) is administered.

B3: The method according to item B1 or B2, wherein the cell proliferative disorder is cancer.

B4: The method according to any one of items B1 to B3, wherein the cell proliferative disorder is a KRAS mutant cancer.

B5: The method according to any one of items B1 to B4, wherein the cell proliferative disorder is a solid cancer.

B6: The method according to any one of items B1 to B5, wherein the dose per administration in step (a) is 3.2 mg.

B7: The method according to item B6, wherein the method comprises, prior to step (a):

(1) administering said compound or salt twice weekly at a dose of 3.2 mg per administration; or
(2)
(2a) administering said compound or salt twice weekly for 3 weeks at a dose of 4 mg per administration,
(2b) pausing administration of said compound or salt for the following 1 week, and
(2c) subsequently repeating steps (2a) and (2b) at least once.

B8: The method according to item B7, wherein the method comprises, prior to step (1) or (2), administering said compound or salt twice weekly at a dose of 4 mg per administration.

B9: The method according to any one of items B1 to B5:
(R1) wherein the method comprises:
(A) first, administering said compound or salt twice weekly at a dose of 4 mg per administration,
(B1) next, administering said compound or salt twice weekly at a dose of 3.2 mg per administration, and
(C) then:
(Ca) administering said compound or salt twice weekly for 3 weeks at a dose of 3.2 mg per administration,
(Cb) pausing administration of said compound or salt for the following 1 week, and
(Cc) subsequently repeating steps (Ca) and (Cb) at least once; or
(R2) wherein the method comprises:
(A) first, administering said compound or salt twice weekly at a dose of 4 mg per administration, and
(B2) next:
(B2a) administering said compound or salt twice weekly for 3 weeks at a dose of 4 mg per administration,
(B2b) pausing administration of said compound or salt for the following 1 week, and
(B2c) subsequently repeating steps (B2a) and (B2b) at least once; or
(R3) wherein the method comprises:
(A) first, administering said compound or salt twice weekly at a dose of 4 mg per administration,
(B2) next:
(B2a) administering said compound or salt twice weekly for 3 weeks at a dose of 4 mg per administration,
(B2b) pausing administration of said compound or salt for the following 1 week, and
(B2c) subsequently repeating steps (B2a) and (B2b) at least once, and
(C) then:
(Ca) administering said compound or salt twice weekly for 3 weeks at a dose of 3.2 mg per administration,
(Cb) pausing administration of said compound or salt for the following 1 week, and
(Cc) subsequently repeating steps (Ca) and (Cb) at least once.

B10: The method according to any one of items B1 to B4, wherein the cell proliferative disorder is multiple myeloma.
B11: The method according to item B10, wherein the dose per administration in step (a) is 4 mg.
B12: The method according to item B10 or B11, wherein the cell proliferative disorder is an NRAS mutant cancer.
B13: The method according to any one of items B10 to B12, wherein said compound or salt is used in combination with dexamethasone, and wherein the method comprises administering said compound or salt before, simultaneously with or after administration of dexamethasone.
B14: The method according to item B13, wherein dexamethasone is administered once weekly at a dose of 20 mg per administration.

B15: The method according to any one of items B1 to B14, wherein the administration of said compound or salt is oral administration.

According to the present invention, there are also provided uses according to the following items C1 to C15.

C1: Use of a compound represented by formula (I):

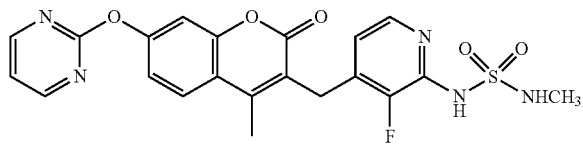

or a pharmaceutically acceptable salt thereof for the manufacture of a medicament for the treatment or prevention of a cell proliferative disorder, wherein the medicament is used in such a manner that:
(a) said compound or salt is administered twice weekly for 3 weeks,
(b) administration of said compound or salt is paused for the following 1 week, and
(c) steps (a) and (b) are subsequently repeated at least once.

C2: The use according to item C1, which is use of a potassium salt of a compound represented by formula (I).
C3: The use according to item C1 or C2, wherein the cell proliferative disorder is cancer.
C4: The use according to any one of items C1 to C3, wherein the cell proliferative disorder is a KRAS mutant cancer.
C5: The use according to any one of items C1 to C4, wherein the cell proliferative disorder is a solid cancer.
C6: The use according to any one of items C1 to C5, wherein the dose per administration in step (a) is 3.2 mg.
C7: The use according to item C6, wherein the medicament is used in such a manner that prior to step (a):
(1) said compound or salt is administered twice weekly at a dose of 3.2 mg per administration; or
(2)
(2a) said compound or salt is administered twice weekly for 3 weeks at a dose of 4 mg per administration,
(2b) administration of said compound or salt is paused for the following 1 week, and
(2c) steps (2a) and (2b) are subsequently repeated at least once.

C8: The use according to item C7, wherein the medicament is used in such a manner that prior to step (1) or (2), said compound or salt is administered twice weekly at a dose of 4 mg per administration.

C9: The use according to any one of items C1 to C5:
(R1) wherein the medicament is used in such a manner that:
(A) first, said compound or salt is administered twice weekly at a dose of 4 mg per administration,
(B1) next, said compound or salt is administered twice weekly at a dose of 3.2 mg per administration,
(C) after which:
(Ca) said compound or salt is administered twice weekly for 3 weeks at a dose of 3.2 mg per administration,
(Cb) administration of said compound or salt is paused for the following 1 week, and
(Cc) steps (Ca) and (Cb) are subsequently repeated at least once; or (R2) wherein the medicament is used in such a manner that:
(A) first, said compound or salt is administered twice weekly at a dose of 4 mg per administration,
(B2) following which:
(B2a) said compound or salt is administered twice weekly for 3 weeks at a dose of 4 mg per administration,
(B2b) administration of said compound or salt is paused for the following 1 week, and
(B2c) steps (B2a) and (B2b) are subsequently repeated at least once; or
(R3) wherein the medicament is used in such a manner that:
(A) first, said compound or salt is administered twice weekly at a dose of 4 mg per administration,
(B2) following which:
(B2a) said compound or salt is administered twice weekly for 3 weeks at a dose of 4 mg per administration,
(B2b) administration of said compound or salt is paused for the following 1 week, and
(B2c) steps (B2a) and (B2b) are subsequently repeated at least once,
(C) after which:
(Ca) said compound or salt is administered twice weekly for 3 weeks at a dose of 3.2 mg per administration,
(Cb) administration of said compound or salt is paused for the following 1 week, and
(Cc) steps (Ca) and (Cb) are subsequently repeated at least once.
C10: The use according to any one of items C1 to C4, wherein the cell proliferative disorder is multiple myeloma.
C11: The use according to item C10, wherein the dose per administration in step (a) is 4 mg.
C12: The use according to item C10 or C11, wherein the cell proliferative disorder is an NRAS mutant cancer.
C13: The use according to any one of items C10 to C12, wherein the medicament is used in combination with dexamethasone, and wherein the medicament is used in such a manner that said compound or salt is administered before, simultaneously with or after administration of dexamethasone.
C14: The use according to item C13, wherein dexamethasone is administered once weekly at a dose of 20 mg per administration.
C15: The use according to any one of items C1 to C14, wherein the administration of said compound or salt is oral administration.

The dosing regimen that is used in the present invention comprises repeating a cycle comprising a prescribed rest period, and makes it possible to administer compound (I) or a salt thereof for long periods while minimizing side effects and maintaining the drug efficacy. In addition, the dosing regimen makes it possible to treat or prevent cell proliferative disorders, particularly cancer, while minimizing the burden on patients.

Advantageous Effects of Invention

According to the present invention, there is provided a dosing regimen for compound (I) or a salt thereof that can be implemented safely and for long periods, as well as a therapeutic or prophylactic medicament for a cell proliferative disorder (particularly cancer) that is used based on such a dosing regimen.

DESCRIPTION OF EMBODIMENTS

Figure 1:
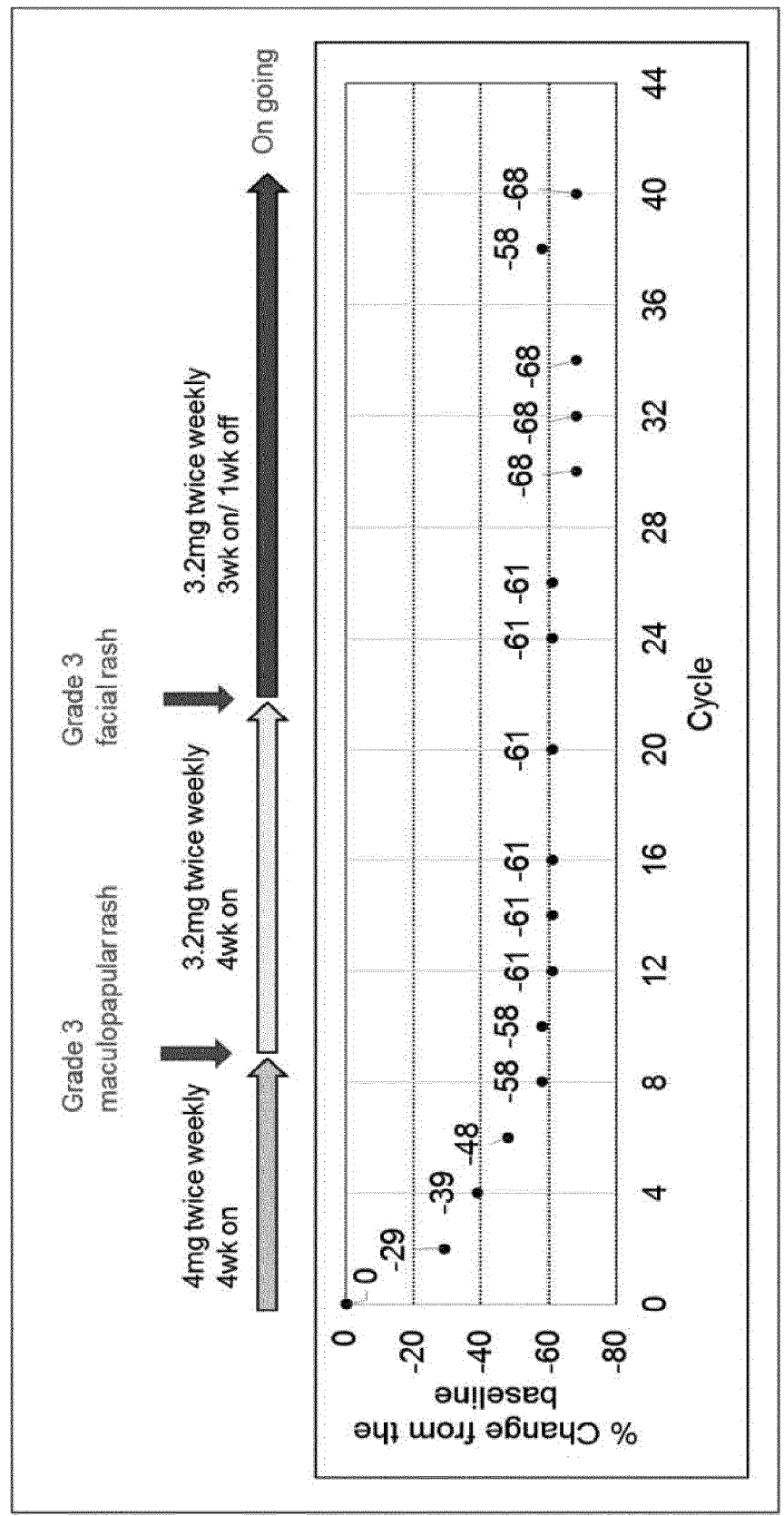
FIG. 1 is a graph showing change in tumor size over time in a KRAS mutant non-small-cell lung cancer patient who received treatment by the medicament of the present invention. The horizontal axis (X-axis) represents the treatment cycle number and the vertical axis (Y-axis) represents the rate of change of tumor size from baseline. The tumor size was measured by CT scan.

Exemplary embodiments of the present invention are described below.

Compound (I) and salts thereof can be prepared by the method described in WO 2007/091736 or WO 2013/035754.

The active ingredient to be used in the present invention is preferably a pharmaceutically acceptable salt of compound (I). Examples of such salts include: inorganic acid salts such as hydrochlorides, hydrobromides, hydroiodides, sulfates and phosphates; sulfonates such as methanesulfonates, benzenesulfonates and toluenesulfonates; carboxylates such as formates, acetates, oxalates, maleates, fumarates, citrates, malates, succinates, malonates, gluconates, mandelates, benzoates, salicylates, fluoroacetates, trifluoroacetates, tartrates, propionates and glutarates; alkali metal salts such as lithium salts, sodium salts, potassium salts, cesium salts and rubidium salts; alkaline earth metal salts such as magnesium salts and calcium salts; and ammonium salts such as ammonium salts, alkylammonium salts, dialkylammonium salts, trialkylammonium salts and tetraalkylammonium salts. Among them, alkali metal salts such as lithium salts, sodium salts, potassium salts, cesium salts and rubidium salts are preferred, sodium salts and potassium salts are more preferred, and potassium salts are particularly preferred. Specific examples of potassium salts of compound (I) include a salt represented by the following formula (Ia).

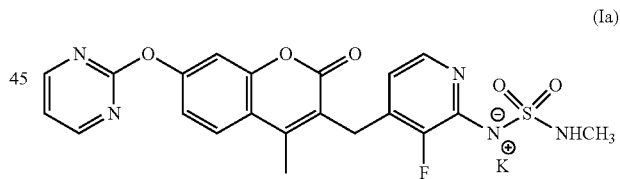

Examples of cell proliferative disorders to be treated or prevented by the medicament or method of the present invention include cancer, rheumatism and inflammation, among which cancer is preferred.

Examples of cancers include: blood and lymphoid cancers, such as leukemias (acute myelocytic leukemia, acute lymphocytic leukemia, chronic myelocytic leukemia, chronic lymphocytic leukemia, and the like), malignant lymphomas (Hodgkin's disease, non-Hodgkin's lymphoma, and the like), multiple myeloma, and myelodysplastic syndrome; central nervous system cancers, such as brain tumor and glioma; and solid cancers, such as head and neck cancers (pharyngeal cancer, laryngeal cancer, tongue cancer, and the like), esophageal cancer, gastric cancer, colorectal cancer (cecal cancer, colon cancer, rectal cancer, or the like), lung cancer (small cell lung cancer, non-small cell lung cancer, or the like), thyroid cancer, breast cancer, gallbladder cancer, pancreatic cancer, liver cancer, prostate cancer, ovarian cancer, uterine cancer (endometrial cancer, cervical cancer, or the like), testicular cancer, renal cell carcinoma, bladder cancer, renal pelvic and ureteral cancer, malignant melanoma, and skin cancer (basal cell carcinoma, squamous cell carcinoma, Paget's disease affecting the scrotum and penis, Merkel cell carcinoma, sweat gland carcinoma (for example, apocrine adenocarcinoma or eccrine adenocarcinoma), sebaceous carcinoma, trichoepithelioma, or the like). A preferred blood or lymphoid cancer is multiple myeloma. Examples of preferred solid cancers include ovarian cancer, breast cancer, uterine cancer, colorectal cancer, and lung cancer, among which non-small cell lung cancer is particularly preferred. Preferred cancers are multiple myeloma and solid cancers, among which multiple myeloma and non-small cell lung cancer are particularly preferred.

The cancer may be one with a gene mutation or without a gene mutation, or one where the presence or absence of mutation is unclear, but it is preferably one with a gene mutation. Examples of genes to be mutated include EGFR, FGFR, ALK, ROS1, PI3K, BRAF, HRAS, KRAS and NRAS. The cancer is preferably a KRAS mutant and/or NRAS mutant one, and more preferably it is KRAS mutant and NRAS mutant multiple myeloma or a KRAS mutant solid cancer (particularly non-small-cell lung cancer). Examples of preferred cancers with gene mutations also include HRAS mutant apocrine adenocarcinoma.

The subject to be administered compound (I) or a salt thereof is an animal, preferably a mammal (for example, a mouse, a rat, a rabbit, a dog, a monkey (for example, a cynomolgus monkey), or a human), and most preferably a human. The human may be an adult (18 years or older) or a child (younger than 18). In the case of a child, it is preferably one of age at least 6 months or older, for example.

With regard to the route of administration to a subject, there may be used: systemic administration such as oral administration, rectal administration, intravenous administration, intramuscular administration, subcutaneous administration, intracisternal administration, vaginal administration, intraperitoneal administration, intravesical administration or inhalation administration; or topical administration in the form of an ointment, gel, cream or the like. Oral administration is preferred.

Compound (I) or a salt thereof is generally prepared as a certain formulation (dosage form). The formulation may be, for example, a tablet, a capsule, a granule, a powder, a fine granule, a pill, or an aqueous or nonaqueous solution or suspension. The solution or suspension may be stored filled in a container suited for the preparation of an individual dose.

Each of such formulations as the ones mentioned above may be produced by a known method, by mixing the compound (I) or salt thereof with a pharmaceutically acceptable additive. Examples of such additives include excipients, lubricants (coating agents), binders, disintegrants, stabilizers, flavoring agents, bases, dispersants, diluents, surfactants, emulsifiers, and the like.

Examples of excipients include starches (starch, potato starch, maize starch and the like), lactose, crystalline cellulose, and calcium hydrogen phosphate.

Examples of lubricants (coating agents) include ethyl cellulose, hydroxypropyl cellulose, hydroxypropylmethyl cellulose, shellac, talc, carnauba wax, and paraffin.

Examples of binders include polyvinylpyrrolidone and macrogol, as well as the same compounds as mentioned for the excipient.

Examples of disintegrants include chemically modified starches and celluloses, such as croscarmellose sodium, sodium carboxymethyl starch, and crosslinked polyvinylpyrrolidone, as well as the same compounds as mentioned for the excipient.

Examples of stabilizers include: paraoxybenzoic acid esters such as methylparaben and propylparaben; benzalkonium chloride; phenols such as phenol and cresol; thimerosal; dehydroacetic acid; and sorbic acid.

Examples of flavoring agents include sweeteners, acidulants and fragrances which are commonly used.

Examples of bases include: fats such as lard; vegetable oils such as olive oil and sesame oil; higher alcohols such as stearyl alcohol and cetanol; animal oils; lanolin acid; vaseline; paraffins; bentonite; glycerine; and glycol oils.

Examples of dispersants include cellulose derivatives (gum arabic, tragacanth, methyl cellulose and the like), stearic acid polyesters, sorbitan sesquioleate, aluminum monostearate, sodium alginate, polysorbates, and sorbitan fatty acid esters.

Examples of solvents and diluents in liquid formulations include phenol, chlorocresol, purified water and distilled water.

Examples of surfactants and emulsifiers include polysorbate 80, polyoxyl 40 stearate, and lauromacrogol.

The preferred percentage of the compound (I) or salt thereof contained in the formulation will differ depending on the dosage form, but it is generally 0.01% to 100% by weight with respect to the total weight of the formulation.

The content of the compound (I) or salt thereof in the formulation may be set as appropriate for the predetermined dosage. The preferred content is 0.01 mg to 10 mg, for example; for a capsule, it may be 0.1 mg to 4 mg, for example. A more preferred content is 0.8 mg, for example.

According to the dosing regimen that is used in the present invention, compound (I) or a salt thereof is administered in the following manner:
  (a) the compound (I) or salt thereof is administered twice weekly for 3 weeks,
  (b) administration of the compound (I) or salt thereof is paused for the following 1 week, and
  (c) steps (a) and (b) are subsequently repeated at least once.

In the present invention, to be administered "twice weekly" means that the compound (I) or salt thereof is administered two times during a one-week period. Administration may be performed twice on the same day, or once a day on different days (which may be consecutive), but it is preferably performed on different days. More preferably, administration is performed on the 1st and 4th days or the 3rd and 6th days of the period, for example, so that the compound (I) or salt thereof is administered at dose intervals as uniform as possible, i.e., at dose intervals of 3 to 4 days. The one-week period may start on a Monday, for example, or it may start on a Wednesday, for example. When two administrations are performed on different days, each may be performed at any time of day, but they are preferably performed at the same time of day (for example, after breakfast).

The dose of the compound (I) or salt thereof per administration is preferably 3.2 mg or 4 mg. When the cancer is multiple myeloma, the dose is preferably 4 mg, and when the cancer is a solid cancer (particularly non-small-cell lung cancer), it is preferably 3.2 mg or 4 mg.

The 4-week cycle consisting of steps (a) and (b) is repeated two times (8 weeks) to 60 times (approximately 4 years and 8 months), for example, and more specifically, it is repeated 8 times (32 weeks) or 18 times (72 weeks), for example. Even if the number of cycles to be repeated has previously been determined, the number of cycles may be changed based on the judgment of the physician or veterinarian depending on, for example, the condition of the subject. Moreover, administration may even be stopped during the cycle based on the judgment of the physician or veterinarian depending on, for example, the condition of the subject.

In one embodiment, prior to step (a):
(1) the compound (I) or salt thereof is administered twice weekly at a dose of 3.2 mg per administration; or
(2)
(2a) the compound (I) or salt thereof is administered twice weekly for 3 weeks at a dose of 4 mg per administration,
(2b) administration of the compound (I) or salt thereof is paused for the following 1 week, and
(2c) steps (2a) and (2b) are subsequently repeated at least once.

Moreover, optionally, prior to step (1) or (2),
(3) the compound (I) or salt thereof is administered twice weekly at a dose of 4 mg per administration.

The cell proliferative disorder to be treated or prevented based on the dosing regimen of this embodiment is preferably a solid cancer and more preferably non-small-cell lung cancer.

In step (1), a cycle consisting of 4 weeks of administration is usually repeated two times (8 weeks) to 30 times (approximately 2 years and 4 months), and it is preferably repeated 13 times (52 weeks), for example.

In step (3), a cycle consisting of 4 weeks of administration is usually repeated two times (8 weeks) to 30 times (approximately 2 years and 4 months), and it is preferably repeated 8 times (32 weeks), for example.

In steps (1) and (3), even if the number of cycles to be repeated has previously been determined, the number of cycles may be changed based on the judgment of the physician or veterinarian depending on, for example, the condition of the subject. Moreover, administration may even be stopped during the cycle based on the judgment of the physician or veterinarian depending on, for example, the condition of the subject.

In one embodiment, compound (I) or a salt thereof is administered in the following manner:
(R1)
(A) First, the compound (I) or salt thereof is administered twice weekly at a dose of 4 mg per administration,
(B1) next, the compound (I) or salt thereof is administered twice weekly at a dose of 3.2 mg per administration,
(C) after which:
(Ca) the compound (I) or salt thereof is administered twice weekly for 3 weeks at a dose of 3.2 mg per administration,
(Cb) administration of the compound (I) or salt thereof is paused for the following 1 week, and
(Cc) steps (Ca) and (Cb) are subsequently repeated at least once; or
(R2)
(A) First, the compound (I) or salt thereof is administered twice weekly at a dose of 4 mg per administration,
(B2) following which:
(B2a) the compound (I) or salt thereof is administered twice weekly for 3 weeks at a dose of 4 mg per administration,
(B2b) administration of the compound (I) or salt thereof is paused for the following 1 week, and
(B2c) steps (B2a) and (B2b) are subsequently repeated at least once; or
(R3)
(A) First, the compound (I) or salt thereof is administered twice weekly at a dose of 4 mg per administration,
(B2) following which:
(B2a) the compound (I) or salt thereof is administered twice weekly for 3 weeks at a dose of 4 mg per administration,
(B2b) administration of the compound (I) or salt thereof is paused for the following 1 week, and
(B2c) steps (B2a) and (B2b) are subsequently repeated at least once,
(C) after which:
(Ca) the compound (I) or salt thereof is administered twice weekly for 3 weeks at a dose of 3.2 mg per administration,
(Cb) administration of the compound (I) or salt thereof is paused for the following 1 week, and
(Cc) steps (Ca) and (Cb) are subsequently repeated at least once.

Figure 3:
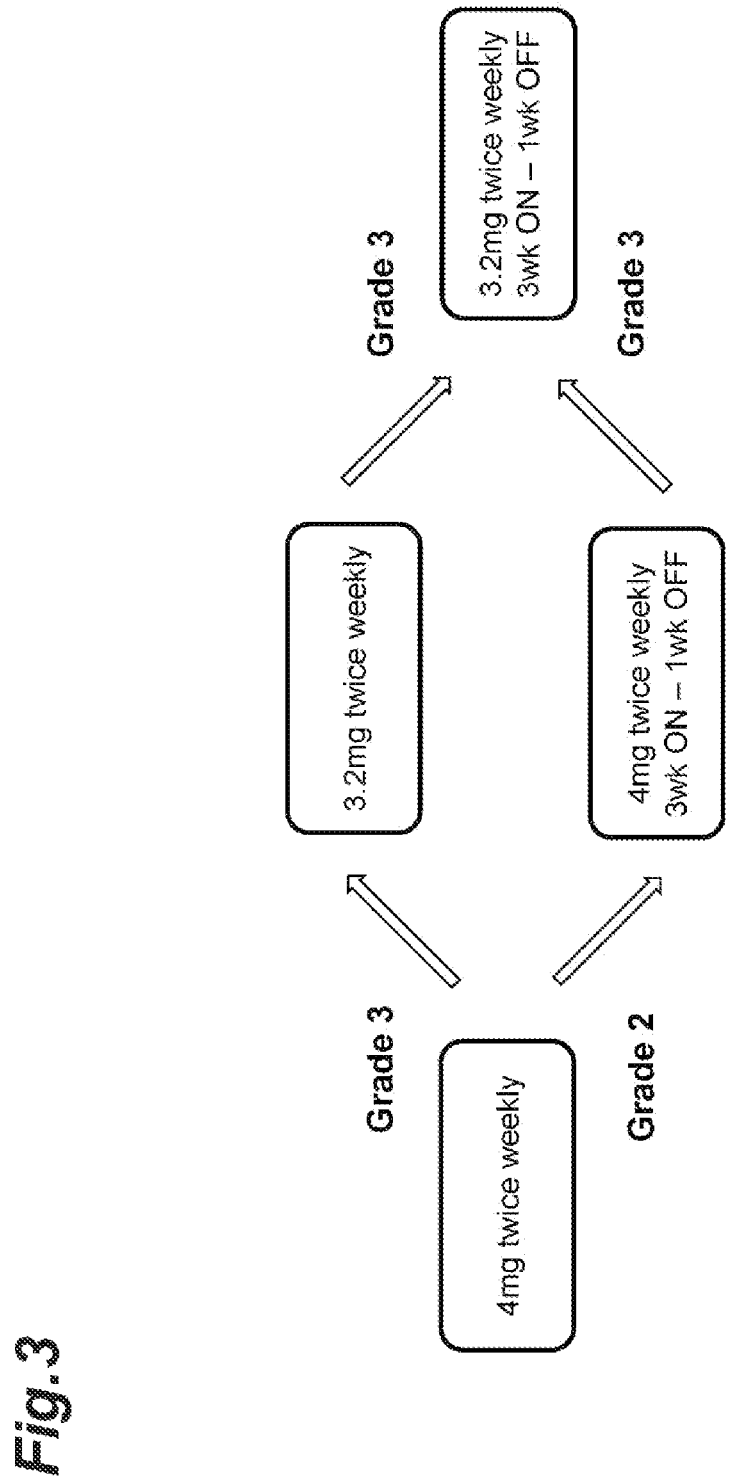
FIG. 3 shows an example of a dosing guidance for the medicament of the present invention.

Which of (R1) to (R3) should be selected may be determined according to, for example, the dosing guidance shown in FIG. 3 depending on, for example, the severity or grade of an adverse event observed in the subject.

The cell proliferative disorder to be treated or prevented based on the dosing regimen of this embodiment is preferably cancer and more preferably a solid cancer. Among solid cancers, non-small cell lung cancer is preferred, and KRAS mutant non-small cell lung cancer is particularly preferred.

In step (A), a cycle consisting of 4 weeks of administration is usually repeated two times (8 weeks) to 30 times (approximately 2 years and 4 months), and it is preferably repeated 13 times (52 weeks), for example.

In step (B1), a cycle consisting of 4 weeks of administration is usually repeated two times (8 weeks) to 30 times (approximately 2 years and 4 months), and it is preferably repeated 8 times (32 weeks), for example.

In steps (A), (B1), (B2) and (C), even if the number of cycles to be repeated has previously been determined, the number of cycles may be changed based on the judgment of the physician or veterinarian depending on, for example, the condition of the subject. Moreover, administration may even be stopped during the cycle based on the judgment of the physician or veterinarian depending on, for example, the condition of the subject.

Compound (I) or a salt thereof may be used either alone or in combination with another drug. When used in combination with another drug, the other drug may be an antiemetic drug or anticancer agent, for example, and is preferably an anticancer agent. Examples of anticancer agents include thalidomide-based anticancer agents such as thalidomide and lenalidomide, proteasome inhibitors such as bortezomib and ixazomib, and steroidal anticancer agents such as dexamethasone and prednisolone.

When the cancer is non-small-cell lung cancer, for example, compound (I) or a salt thereof is preferably used alone.

When compound (I) or a salt thereof is used for treatment of multiple myeloma in combination with another drug, the other drug is preferably dexamethasone, for example. Dexamethasone is a drug that is part of the standard of care for multiple myeloma.

When compound (I) or a salt thereof is used for treatment of multiple myeloma in combination with dexamethasone, dexamethasone is preferably administered once weekly and the dose of dexamethasone per administration is preferably, for example, 20 mg.

When compound (I) or a salt thereof is used in combination with dexamethasone, the order and timing of their administrations are not particularly restricted, and the compound (I) or salt thereof may be administered before, simultaneously with or after administration of dexamethasone. For example, in step (a), when the compound (I) or salt thereof and dexamethasone are administered in a one-week period, it is preferred, for example, that: the compound (I) or salt thereof is administered on the 1st and 4th days and dexamethasone on the 2nd day of the period, or the compound (I) or salt thereof is administered on the 3rd and 6th days and dexamethasone on the 4th day of the period, or the compound (I) or salt thereof is administered on the 2nd and 5th days and dexamethasone on the 1st day of the period, or the compound (I) or salt thereof is administered on the 4th and 7th days and dexamethasone on the 2nd day of the period. The one-week period may start on a Monday, for example, or it may start on a Wednesday, for example. Each administration may be performed at any time of day, but the administrations are preferably performed at the same time of day (for example, after dinner).

The period during which the compound (I) or salt thereof is used in combination with dexamethasone may be determined based on the judgment of the physician or veterinarian depending on, for example, the condition of the subject. Also, administration of either or both the compound (I) or salt thereof and dexamethasone may be stopped based on the judgment of the physician or veterinarian depending on, for example, the condition of the subject.

A medicament for the treatment or prevention of a cell proliferative disorder that comprises a compound represented by formula (I):

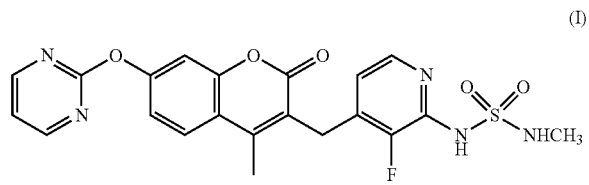 [SMILES: CNS(=O)(=O)Nc1nccc(Cc2c(C)c3ccc(Oc4ncccn4)cc3oc2=O)c1F]

(I)

or a pharmaceutically acceptable salt thereof as an active ingredient may be packaged together with:
(i) a container for housing the medicament, and
(ii) an instruction(s) for using the medicament in such a manner that:
(a) the compound (I) or salt thereof is administered twice weekly for 3 weeks,
(b) administration of the compound (I) or salt thereof is paused for the following 1 week, and
(c) steps (a) and (b) are subsequently repeated at least once.

It is preferred, for example, that the packaged medicament is a medicament according to any one of items A1 to A15 above and that the instruction(s) above is/are an instruction(s) for using the medicament in such a manner that the compound (I) or salt thereof is administered according to the prescribed dosing regimen corresponding to the medicament used. The phrase "prescribed dosing regimen corresponding to the medicament used" means, in the case of the medicament of item A9, for example, any of the dosing regimens (R1) to (R3) prescribed in item A9.

The packaging may be performed using a packaging material (such as a carton), for example. The package may also include a label, a pamphlet or a pharmaceutically acceptable cushioning material, for example.

The container of (i) above is, for example, a bottle or a PTP sheet, and it may be produced from a material such as glass, plastic or aluminum, for example. Preferably, the container is printed with letters indicating, for example, that the medicament is to be used for treatment or prevention of the prescribed disease, or it has a label attached on which such letters are printed.

The medicament may or may not be housed in the container of (i), but is preferably housed in it.

The instruction(s) of (ii) above include(s) information necessary for use of the medicament based on the prescribed dosing regimen. The instruction(s) may also include information relating to the efficacy and effects of the medicament, for example.

The instruction(s) of (ii) may be in the form of a document, for example. The document containing the instruction(s) may be a package insert, for example. The document containing the instruction(s) may also be printed on a label, or printed on a packaging material (such as a carton), for example. The instruction(s) may also be in the form of printing on paper or plastic, for example, or in the form of electronic storage in a storage medium such as a CD-ROM or flash memory.

EXAMPLES

Exemplary embodiments of the present invention are described below based on examples.

Example 1

A potassium salt of compound (I) (the potassium salt being also referred to as the "IMP" in this example) was orally administered to a patient with KRAS mutant and NRAS mutant IgG lambda multiple myeloma at a dose of 4 mg twice weekly (Tuesday and Friday) in 4-week cycles consisting of 3 weeks of treatment followed by 1 week of rest (3 weeks on/1 week off). Dexamethasone was not used in combination with the IMP.

The patient started dosing on 29 Nov., 2016. His initial and ongoing toxicity was intermittent Grade 1 diarrhoea that may be related to the IMP. He also had a Grade 2 rash related to the IMP. He had been faring very well since, with an ongoing partial response as per the international myeloma working group (IMWG) criteria (FLCk: 325 mg/L (pre), 161 mg/L (after 1 cycle), and 264 mg/L (after 2 cycles)).

The patient had previously been treated with:
Autologous stem cell transplant
Proteasome inhibitor
Immunomodulatory drug
Cyclophosphamide+Dexamethasone+Thalidomide
Melphalan
Lenalidomide
Cyclophosphamide+Bortezomib
Dexamethasone
Spine T3-T12, 5 fractions (radiotherapy)

Example 2

A potassium salt of compound (I) (the potassium salt being also referred to as the "IMP" in this example) was orally administered to a patient with KRAS mutant non-small-cell lung cancer.

The patient started treatment on 1 Sep., 2014. The IMP was first administered at a dose of 4 mg twice weekly in 4-week cycles consisting of 4 weeks of treatment (4 mg 4 wk on). In Cycle 9, due to Grade 3 maculopapular rash, the dosage was reduced to 3.2 mg twice weekly in 4-week cycles (3.2 mg 4 wk on). In Cycle 22, due to Grade 3 facial rash, the dosage was reduced again to a 3 weeks on/1 week off schedule with 3.2 mg twice weekly (3.2 mg 3 wk on/1 wk off). These reductions resulted in a reduction of their rash, which was only Grade 1 and being managed well with responding with a maintained partial response (PR) by Response Evaluation Criteria in Solid Tumors (RECIST) 1.1 at Cycle 40.

The change in tumor size in the patient over the first 40 cycles (approximately 3 years) is shown in FIG. 1. The horizontal axis (X-axis) represents the treatment cycle number and the vertical axis (Y-axis) represents the rate of change of tumor size from baseline. The tumor size was measured by CT scan. The best responses of the dosing schedules 4 mg 4 wk on, 3.2 mg 4 wk on, and 3.2 mg 3 wk on/1 wk off were 58% reduction, 61% reduction, and 68% reduction in target lesions by RECIST 1.1, respectively. Treatment of the patient by the IMP is being continued as of 18 Apr., 2018 (at Cycle 48, equivalent to 3.6 years) without any Grade 2 or higher rash being observed.

The patient had previously been treated with:
Carboplatin/Pemetrexed
Pemetrexed
Docetaxel
Pleurodesis (October 2012) (surgery)

Example 3

A potassium salt of compound (I) (the potassium salt being also referred to as the "IMP" in this example) was orally administered to a patient with HRAS mutant apocrine adenocarcinoma of the scalp. Apocrine adenocarcinoma of the scalp is a cutaneous sweat gland carcinoma. The patient was diagnosed in 2014, and had radiotherapy and surgery twice before treatment with the IMP.

Treatment of the patient by the IMP was started on 8th Jan., 2018 at a dose of 4 mg twice weekly in 4-week cycles. In Cycle 1 Week 3, the patient had Grade 2 acneiform rash and Grade 2 diarrhoea and thus the dosage was reduced to a 3 weeks on/1 week off schedule with 4 mg twice weekly. The grade of acneiform rash was one (1) in Cycle 2 Day 1, three (3) in Cycle 2 Day 22, and two (2) in Cycle 3 Day 1. Thus, the dose at Cycle 3 Day 1 was not reduced to 3.2 mg and was determined as 4 mg. The change in tumor size in the patient measured by CT scan demonstrated partial response (PR) by Response Evaluation Criteria in Solid Tumors (RECIST) 1.1 (54% reduction at Cycle 2 Day 22 and 58% reduction at Cycle 4 Day 15).

Figure 2:
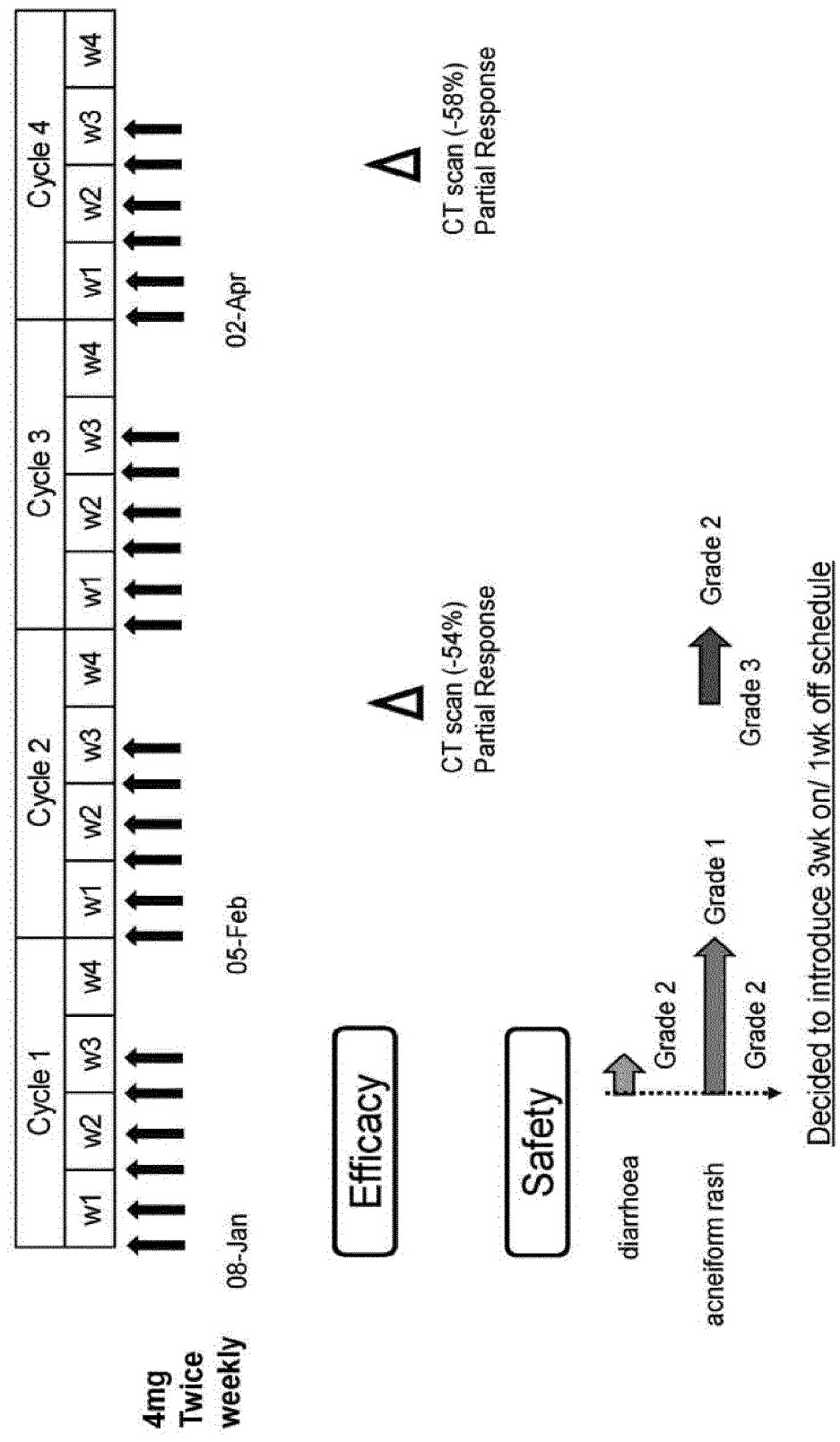
FIG. 2 summarizes: a dosing regimen that was used for a HRAS mutant apocrine adenocarcinoma patient; and the observed efficacy and safety of the dosing regimen.

The dosing regimen used in this example and the observed efficacy and safety thereof are summarized in FIG. 2. The dosing guidance used in this example is shown in FIG. 3. Treatment of the patient by the IMP is ongoing as of 30th Apr., 2018 (Cycle 5 Day 1) without any Grade 2 or higher rash or diarrhoea being observed.

According to the dosing guidance shown in FIG. 3, treatment of a subject is started at 4 mg twice weekly.

If a drug-related adverse event (e.g., skin rash, diarrhoea, or creatine phosphokinase (CPK) elevation) of Grade 3 occurs after the start of treatment, the dose level is reduced to 3.2 mg twice weekly. If the subject experiences a drug-related Grade 3 adverse event despite the reduction in the dose level, the dose intensity can be reduced to 3.2 mg twice weekly on a 3 weeks on/1 week off schedule.

If a drug-related adverse event (e.g., skin rash, diarrhoea, or CPK elevation) of Grade 2 occurs after the start of treatment, the dose intensity is reduced to 4 mg twice weekly on a 3 weeks on/1 week off schedule. If the subject experiences a drug-related Grade 3 adverse event despite the reduction in the dose intensity, the dose level can be reduced to 3.2 mg twice weekly on a 3 weeks on/1 week off schedule.

If the adverse events improve, the dose level and/or intensity can be reverted to the previous dose level and/or intensity based on the judgment of the physician or veterinarian.

The invention claimed is:

1. A method for the treatment of cancer in a subject in need thereof, wherein the cancer is selected from the group consisting of multiple myeloma, non-small cell lung cancer, ovarian cancer, malignant melanoma, pancreatic cancer, colorectal cancer, brain tumor, glioma, gastric cancer, thyroid cancer, breast cancer, endometrial cancer, and cervical cancer, provided that the cancer is not an HRAS mutant cancer, a KRAS mutant cancer or an NRAS mutant cancer, the method comprising:

(a) administering a compound represented by formula (I):

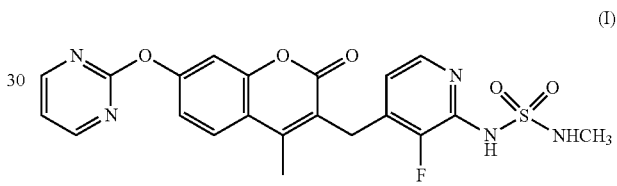

or a pharmaceutically acceptable salt thereof twice weekly for 3 weeks, (b) pausing administration of said compound or salt for the following 1 week, and (c) subsequently repeating steps (a) and (b) at least once.

2. The method according to claim 1, wherein a potassium salt of a compound represented by formula (I) is administered.

3. The method according to claim 1, wherein the dose per administration in step (a) is 3.2 mg.

4. The method according to claim 1, wherein the dose per administration in step (a) is 4 mg.

5. The method according to claim 1, wherein the method comprises, prior to step (a), administering said compound or salt twice weekly at a dose of 3.2 mg per administration for at least 4 weeks.

6. The method according to claim 1, wherein the method comprises, prior to step (a), administering said compound or salt twice weekly at a dose of 4 mg per administration for at least 4 weeks.

7. The method according to claim 1, wherein the administration of said compound or salt is oral administration.

8. The method according to claim 1, wherein the cancer is multiple myeloma.

9. The method according to claim 1, wherein the cancer is non-small cell lung cancer.

10. The method according to claim 1, wherein the cancer is ovarian cancer.

11. The method according to claim 1, wherein the cancer is pancreatic cancer.

12. The method according to claim 1, wherein the cancer is colorectal cancer.

13. The method according to claim 1, wherein the cancer is malignant melanoma.

14. The method according to claim 1, wherein said compound or salt is administered in combination with an anticancer agent.

15. The method according to claim 1, wherein the cancer is brain tumor.

16. The method according to claim 1, wherein the cancer is glioma.

17. The method according to claim 1, wherein the cancer is gastric cancer.

18. The method according to claim 1, wherein the cancer is thyroid cancer.

19. The method according to claim 1, wherein the cancer is breast cancer.

20. The method according to claim 1, wherein the cancer is endometrial cancer.

21. The method according to claim 1, wherein the cancer is cervical cancer.

* * * * *